United States Patent [19]
Zusi et al.

[11] Patent Number: 6,008,251
[45] Date of Patent: Dec. 28, 1999

[54] RETINOID-LIKE COMPOUNDS

[75] Inventors: Fred C. Zusi, Hamden, Conn.; Peter R. Reczek, E. Amherst, N.Y.; Jacek Ostrowski, Getzville, N.Y.

[73] Assignee: Bristol-Myers Squibb Company, Princeton, N.J.

[21] Appl. No.: 09/049,430

[22] Filed: Mar. 27, 1998

[51] Int. Cl.⁶ .................................................. A61K 31/19
[52] U.S. Cl. ........................................ 514/562; 562/457
[58] Field of Search .............................. 514/562; 562/457

[56] References Cited

U.S. PATENT DOCUMENTS

| | | |
|---|---|---|
| 4,703,110 | 10/1987 | Shudo . |
| 4,808,631 | 2/1989 | Klaus . |
| 4,876,381 | 10/1989 | Lang et al. . |
| 5,087,743 | 2/1992 | Janssen et al. . |
| 5,618,839 | 4/1997 | Starrett, Jr. et al. . |

OTHER PUBLICATIONS

L. Nagy, et al, Activation of Retinoid X Receptors Induces Apoptosis in HL–60 Cell Lines, Molecular and Cellular Biology, 15(7), pp. 3540–3551 (1995).

S. M. Lippman, et al, "Retinoids as Preventive and Therapeutic Anticancer Agents (Part I)," Cancer Treatment Reports, 71(4), pp. 391–405 (1987).

S. M. Lippman, et al, "Retinoids as Preventive and Therapeutic Anticancer Agents (Part II)," Cancer Treatment Reports, 71(5), pp. 493–515 (1987).

M. Huang, et al, "Use of All–Trans Retinoic Acid in the Treatment of Acute Promyelocytic Leukemia," Blood, 72(2), pp. 567–572 (1988).

W. K. Hong, et al, "Prevention of Second Primary Tumors with Isotretinoin in Squamous–Cell Carcinoma of the Head and Neck," New England Journal of Medicine, 323(12), pp. 795–801 (1990).

*Primary Examiner*—James H. Reamer
*Attorney, Agent, or Firm*—David M. Morse

[57] ABSTRACT

The present invention relates to a compound of the formula

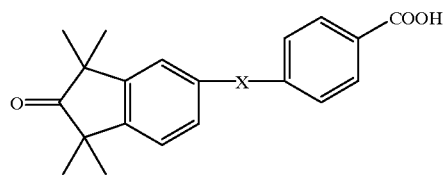

wherein X is —CONH— or —NHCO—, or a nontoxic pharmaceutically acceptable salt, physiologically hydrolyzable ester or solvate thereof.

The compounds of the present invention exhibit retinoid-like properties and are thus useful as antiinflammatory agents for chronic skin inflammatory diseases such as psoriasis and atopic dermatitis, as agents for the treatment of rheumatic diseases such as rheumatoid arthritis, as antitumor agents for the treatment of various tumors, and as agents for the treatment of non-malignant proliferative skin conditions.

7 Claims, No Drawings

RETINOID-LIKE COMPOUNDS

FIELD OF THE INVENTION

The present invention provides compounds having retinoid-like activity. More specifically, the compounds of the present invention are useful as antiinflammatory agents for chronic skin inflammatory diseases such as psoriasis and atopic dermatitis, as agents for the treatment of rheumatic diseases such as rheumatoid arthritis, as antitumor agents for the treatment of various tumors, and as agents for the treatment of non-malignant proliferative skin conditions.

BACKGROUND OF THE INVENTION

Retinoic acids and its natural and synthetic analogs exact a wide variety of biological effects. They have been found to affect cellular growth and differentiation and are promising agents for the treatment of several cancers.

U.S. Pat. No. 4,808,631 discloses compounds of the formula

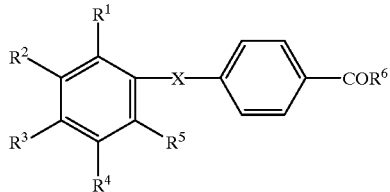

wherein $R^1$, $R^2$, $R^3$, $R^4$, and $R^5$ independently are hydrogen, alkyl, or $C_{3-7}$cycloalkyl or two adjacent residues $R^1$ to $R^5$ taken together with adjacent carbons of the phenyl ring form a 5–7 membered ring optionally substituted by one or more lower alkyl groups; X is —$NR^7$—CO— or —CO—$NR^7$—; $R^6$ is hydroxy, lower alkoxy or —$NR^8R^9$; and $R^7$, $R^8$ and $R^9$, independently, are hydrogen or lower alkyl, and where $R^6$ is hydroxy, their pharmaceutically usable salts for the treatment of inflammatory and rheumatic diseases.

U.S. Pat. No. 4,703,110 discloses compounds of the formula

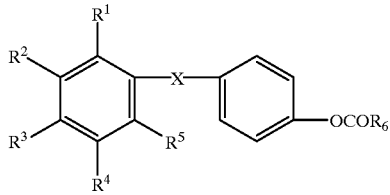

wherein $R_1$, $R_2$, $R_3$, $R_4$ and $R_5$ may be the same or different, each represents hydrogen, middle and lower alkyl and/or cycloalkyl having 3–7 atoms, with the proviso each cannot be hydrogen simultaneously, and both neighboring substituents may be combined with each other to form a ring having 5–12 carbon atoms, $R_6$ represents hydroxyl, lower alkoxyl, lower alkylamino of the formula —$NR_7'R_8'$, wherein $R_7'$ and $R_8'$ each represent hydrogen or lower alkyl, X represents a group of the formula:

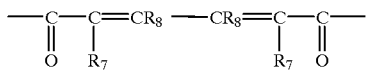

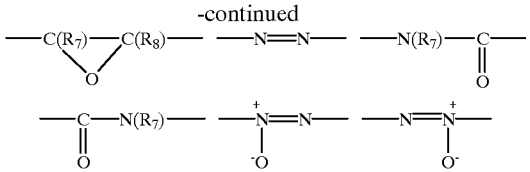

wherein $R_7$ and $R_8$ represent hydrogen or lower alkyl. Such compounds are said to be capable of inducing the differentiation of premalignant and malignant cells to morphologically and functionally mature cells which cannot proliferate further and can therefore be used in the therapy of premalignant and malignant diseases.

SUMMARY OF THE INVENTION

The present invention relates to novel compounds of the formula

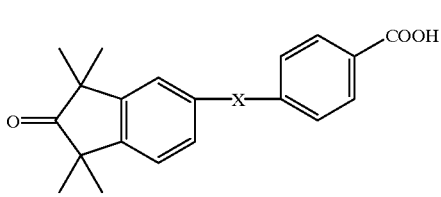

or nontoxic pharmaceutically acceptable salts, physiologically hydrolyzable esters or solvates thereof in which X is —CONH— or —NHCO—. The compounds of the present invention are useful as antiinflammatory agents for treatment of chronic skin inflammatory diseases such as psoriasis and atopic dermatitis, as agents for the treatment of rheumatic diseases such as rheumatoid arthritis, as antitumor agents for the treatment of various tumors, and as agents for the treatment of nonmalignant proliferative skin diseases.

Also provided by the invention are pharmaceutical compositions comprising a therapeutically effective amount of one or more of the compounds of the present invention in combination with a pharmaceutically acceptable excipient.

DETAILED DESCRIPTION OF THE INVENTION

The present invention relates to a compound of the formula

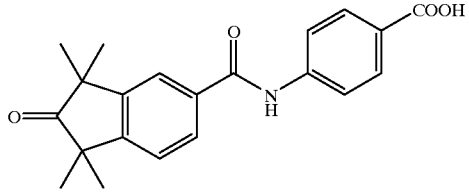

or

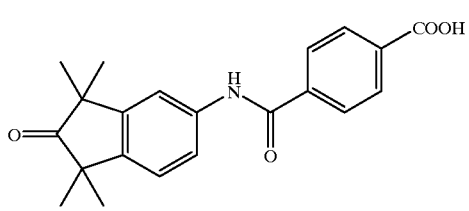

or a nontoxic pharmaceutically acceptable salt, physiologically hydrolyzable ester, or solvate thereof.

Compounds of formula I may form pharmaceutically acceptable metal and amine salts in which the cation does not contribute significantly to the toxicity or biological activity of the salt. These salts are also part of the present invention. Suitable metal salts include the sodium, potassium, calcium, barium, zinc, and aluminum salts. The sodium or potassium salts are preferred. Amines which are capable of forming stable salts group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like pharmaceutically acceptable amines.

The compounds of formula I contain a carboxy group and so can form physiologically hydrolyzable esters which serve as prodrugs by being hydrolyzed in the body to yield formula I compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, benzyl, 4-methoxybenzyl, indanyl, phthalidyl, methoxymethyl, $C_{1-6}$alkanoyloxy, $C_{1-6}$alkyl, e.g. acetoxymethyl, pivaloyloxymethyl or propionyloxymethyl, $C_{1-6}$alkoxycarbonyloxy, $C_{1-6}$alkyl, e.g. methoxycarbonyloxymethyl or ethoxycarbonyloxymethyl, glycyloxymethyl, phenylglycyloxymethyl, (5-methyl-2-oxo-1-3-dioxolen-4-yl)-methyl and other well-known physiologically hydrolyzable esters used, for example, in the penicillin and cephalosporin arts. Such esters are prepared by conventional techniques known in the art.

The structural formulae as drawn in the instant application are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The compounds of the present invention can be made by a variety of methods well-known to those skilled in the art. Examples 1–2 below illustrate one embodiment of their synthesis.

Biological Activity

Antitumor Activity

A representative compound of the present invention, i.e. that of Example 1, was tested for its antitumor activity in the following model system:

HL 60 cells were evaluated for the effect of retinoic acid and the compound of Example 1 on both differentiation and apoptosis end points by the method described in *Molecular and Cellular Biology*, 15, 3540–3551 (1995). Cells were grown in culture for times up to 9 days in the presence of 1 μM all-trans retinoic acid (t-RA) or 1 μM compound of Example 1. At the end of each day of the culture period, cells were washed and stained with NBT (nitro blue tetrazolium) and counted. NBT staining reveals distinct changes in nuclear morphology and can easily be compared with treatment by t-RA or compound of Example 1. The $EC_{50}$ is defined as the culture day necessary to convert cells into a differentiated or apoptosed phenotype and is given below in Table I. The compound of Example 1 is comparable to t-RA in this assay.

TABLE I

Differentiation and Apoptosis of HL60 cells

| Compound | $EC_{50}$ |
| --- | --- |
| all-trans retinoic acid | 3.2 days |
| Example 1 | 4.0 days |

Table II shows the percentage of either differentiated or apoptosed HL60 cells after treatment with all-trans retinoic acid or the compound of Example 1.

TABLE II

| Day | t-RA | Compound of Ex. 1 |
| --- | --- | --- |
| 1 | 21 | 11 |
| 2 | 23 | 22 |
| 3 | 48 | 40 |
| 4 | 80 | 50 |
| 5 | 95 | 61 |
| 6 | 96 | 78 |
| 7 | 97 | 85 |
| 8 | 98 | 95 |
| 9 | 97 | 93 |

Thus, the compounds of the present invention are shown to be useful in the treatment of tumors in mammals.

The compounds of the present invention are also useful for treating a host animal, preferably a mammal and most preferably a human, for chronic skin inflammatory diseases (e.g. psoriasis), rheumatic diseases and non-malignant proliferative skin conditions. In such cases a therapeutic effective amount of a compound of formula I or a pharmaceutical composition thereof is administered to said host animal in the same manner as with other retinoid compounds.

The compounds of formula I above may be used topically or systemically, as anticancer agents and in the treatment, amelioration or prevention of the skin disorders and rheumatic illnesses (including rheumatoid arthritis) described in U.S. Pat. No. 5,618,839. In this regard they may be used for therapy in animals, including humans, of premalignant epithelial cell lesions, as a prophylaxis against tumor promotion in epithelial cells and treatment for dermatoses such as ichthyoses, follicular disorders, benign epithelial disorders and other proliferative skin diseases such as psoriasis, eczema, atopic dermatitis, non-specific dermatosis and the like. They may also be used in reversing and preventing the effects of irradiation damage to skin. When used for the above purposes, they will usually be formulated with a pharmaceutically acceptable liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles (excipients) in the pharmaceutical formulation art. The carrier may be organic or inorganic in nature. Examples of pharmaceutically acceptable carriers that may be used to formulate a compound of formula I are water, gelatin, lactose, starch, mineral oil, cocoa butter, dextrose, sucrose, orbital, mannitol, gum acacia, alginates, cellulose, talc, magnesium stearate, polyoxyethylene sorbitan monolaurate, and other commonly used pharmaceutical carriers. In addition to a compound of formula I and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0.002% to 1% by weight.

For topical administration the compounds of formula I are conveniently provided in the form of unguents, gels, creams, ointments, powders, dyeing compositions, solutions, suspensions, emulsions, lotions, sprays, adhesive plasters and impregnated pads. The compounds according to the invention can be mixed with inert nontoxic, generally liquid or pasty, bases suitable for topical treatment. Preparation of such topical formulations is well described in the art of pharmaceutical formulations as exemplified, for example, in Remington's Pharmaceutical Science, Edition 17, Mack Publishing Company, Easton, Pa. Other medicaments can be added to such formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitable administered at the rate of 100 $\mu$g to 100 mg per day per kg of body weight. The required dose can be administered in one or more portions. For oral administration, suitable forms are, for example, tablets, pills, dragees, syrups, suspensions, emulsions, solutions, powders and granules; a preferred method of administration consists in using pills containing from 1 mg to about 25 mg of active substance.

U.S. Pat. No. 4,876,381 issued on Oct. 24, 1989 to Lang et al. provides examples of formulations constituting gel, unguent, powder, cream, etc. The aforesaid U.S. patent can be used as a guide to formulate a compound of formula I and is herein incorporated by reference in its entirety.

Isotretinoin (Accutane®) and etretinate (Tegison®) are used clinically to treat severe recalcitrant psoriasis, including the erythrodermica and generalized pustular types, respectively. Their mode of use is amply illustrated in the Physicians's Desk Reference, 47th Edition, 1993, published by Medical Economics Data. The compounds of formula I may also be used to treat severe recalcitrant psoriasis. In so doing, the compounds of the present invention may be used in a similar fashion to isotretinoin and etretinate; thus, the relevant sections on isotretinoin and etretinate in the Physician's Desk Reference will serve as a convenient guide which will obviate the need for any undue experimentation.

The compounds according to the invention can also be administered parenterally in the form of solutions or suspensions for intravenous or intramuscular perfusions or injections. In that case, the compounds according to the invention are generally administered at the rate of about 10 $\mu$g to 10 mg per day per kg of body weight; a preferred method of administration consists of using solutions or suspensions containing approximately from 0.01 mg to 1 mg of active substance per ml.

Several retinoids have been found to possess anti-tumor properties. Roberts, A. B. and Sporn, M. B. in "*The Retinoids*", Sporn, M. B., Roberts, A. B., and Goodman, D. S., eds, 1984, 2 pp. 209–286, Academic Press, New York; Lippman, S. M., Kessler, J. F., and Meyskens, F. L., *Cancer Treat. Rep.,* 1987, 71, p. 391; ibid., p. 493. As used herein, the term "anti-tumor" includes both chemopreventative (prophylactic or tumor promotion inhibiting) and therapeutic (curative) use. For example, all-trans retinoic acid can be used to treat acute promyelocytic leukemia. Huang, M. Et al., *Blood,* 1988, 72, p. 567. Isotretinoin has been shown to be useful in prevention of second primary tumors in squamous-cell carcinoma of the head and neck. Hong, W. K. et al., *N. Engl. J. Med.,* 1990, 323, p. 795.

The compounds of formula I can be used in a substantially similar manner to retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula II in squamous-cell carcinoma of the head and neck, an oncologist may refer to the study by Hong, W. K. et al. in *N. Engl. J. Med.,* 1990, 323, p. 795. For treating acute promyelocytic leukemia, the oncologist may refer to the study by Huang, M. et al. in *Blood,* 1988, 72 p. 567.

DESCRIPTION OF SPECIFIC EMBODIMENTS

The specific examples which follow illustrate the synthesis of representative compounds of the present invention. The procedures may be adapted to variations in order to produce compounds within the scope of the invention but not specifically disclosed.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quarter (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value. All melting points were not corrected.

EXAMPLE 1

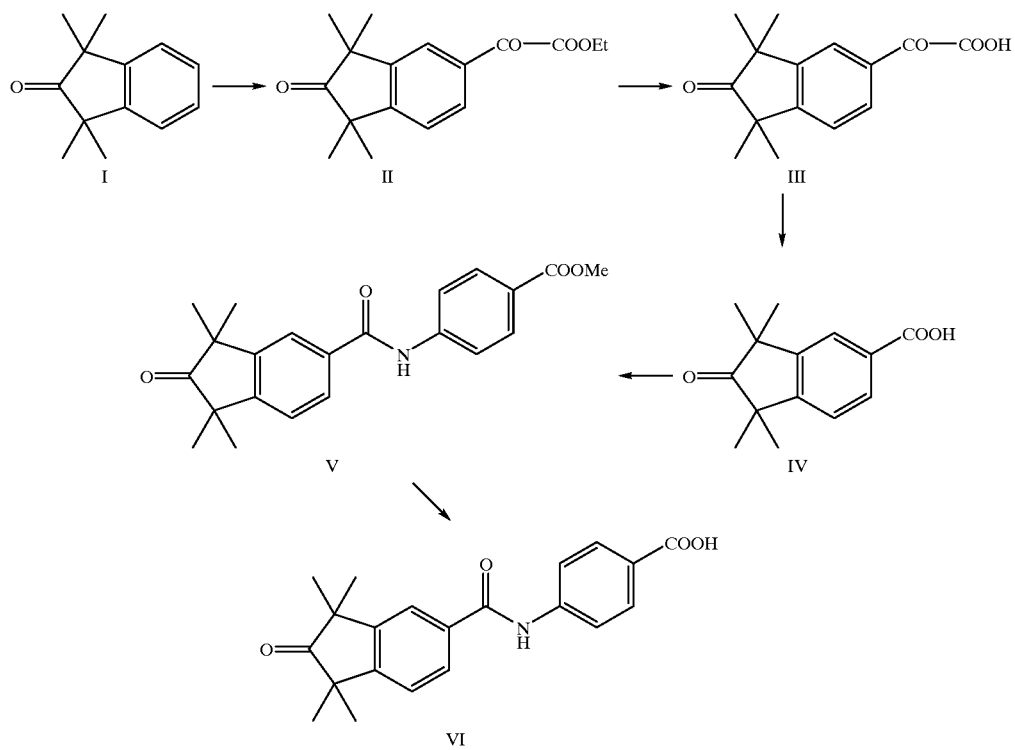

Description of Synthesis

Compound I (1,1,3,3-Tetramethylindan-2-one), is known in the literature (E. Langhals and H Langhals, *Tet Lett* 1990, vol 31, pg 859 and H A Bruson et al, *J Amer Chem Soc* 1958, vol 80, pg 3633). 1 is acylated with ethyl oxalyl chloride/aluminum chloride to give keto-ester II, which is hydrolyzed using base to give keto acid III. III is oxidatively decarboxylated using aqueous hydrogen peroxide to give acid IV, which is activated by conversion to its acid chloride using thionyl chloride and then condensed with commercially available methyl p-aminobenzoate to give amide-ester V. V is then cleaved using hydroxide base to give final product VI.

Compound II—Ethyl 2(1',1',3',3'-tetramethyl-2-keto-indan-5-yl-2-oxoacetate

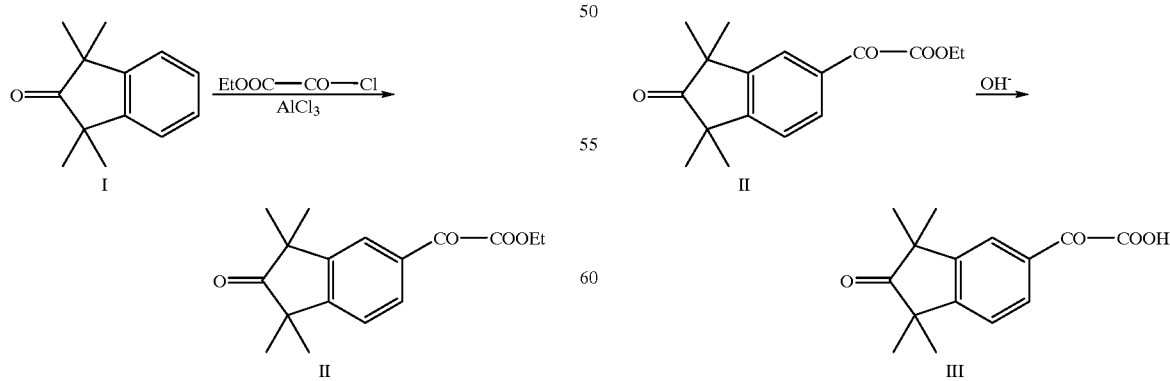

To a stirring suspension of 16.8 gms AlCl$_3$ in 85 mL methylene chloride was added 5 mL ethyl oxalyl chloride. This mixture was stirred at room temperature for ½ hour, then 2.9 gms I was added and the mixture was stirred at room temperature for a further 2 hrs, then poured over ~1 kg crushed ice. The layers were separated after the ice had melted, the aqueous layer was washed with methylene chloride, and the combined organic layers were washed with saturated NaCl solution, dried over MgSO$_4$, filtered, and evaporated. The resulting oil was re-dissolved in ethyl acetate, back-extracted with NaHCO$_3$ solution, dried again, and evaporated to give 2.3 gms yellow/orange oil (II). thin layer chromatography (10% ethyl acetate/hexane on silica gel) shows main component R$_f$ 0.35

Infrared spectrum (NaCl plates): 2969, 1746, 1686, 1184 cm$^{-1}$ NMR (CDCl$_3$): δ7.95 (m, 2H), 7.41 (d, J=8.4, 1H), 4.48 (q, J=7, 2H), 1.44 (t, J=7, 3H), 1.38 (s, 6H), 1.37 (s, 6H)

Compound III—2(1',1',3',3'-Tetramethyl-2'-keto-indan-5'-yl)-2-oxoacetic acid

Compound II (2.3 gms) was dissolved in 200 mL methanol and 50 mL 1 N NaOH was added. This mixture was stirred at room temperature for ½ hour. The solvent was then evaporated, the residue dissolved in water, and the aqueous solution was washed with ethyl acetate. The aqueous phase was next acidified with concentrated HCl and the precipitated solid extracted into ethyl acetate. This organic phase was separated, washed with saturated NaCl solution, dried over MgSO$_4$, filtered, and evaporated to give 1.1 gms III as an orange oil which solidified to a yellow solid. Thin layer chromatography (30% ethyl acetate/hexane+1% formic acid on silica gel) showed the main component at R$_f$ 0.2.

Infrared spectrum (KBr pellet): Broad absorption 3400–2500, 2971, 1751, 1726, 1686, 1611, 1167 cm$^{-1}$ NMR (CDCl$_3$): δ 8.33 (dd, J=8, J=1.74, 1H), 8.26 (d, J=1.68, 1H), 7.44 (d, J=8, 1H), 1.40 (s, 6H), 1.39 (s, 6H)

Compound IV—1,1,3,3-Tetramethyl-2-keto-indan-5-yl)-carboxylic acid

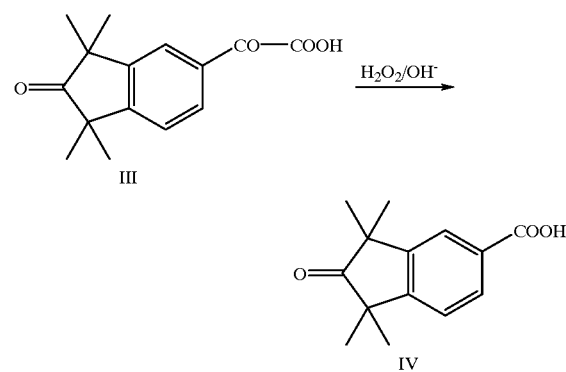

To a solution of 1.1 gms III in 15 mL methanol was added 90 mL 1 N NaOH and 5 mL 30% H$_2$O$_2$, then the mixture was stirred at room temperature overnight. The solution was washed with 65 mL ethyl ether, then was acidified with concentrated HCl, and the precipitated acid extracted into ethyl acetate, which was washed with saturated NaCl solution, dried with MgSO$_4$, filtered, and evaporated to give 1 gm white solid (IV). Thin layer chromatography (30% ethyl acetate/hexane+1% formic acid on silica gel) showed the main component at R$_f$ 0.4.

Infrared spectrum (KBr pellet): Broad absorption 3500–2500, 2970, 1750, 684, 1258 cm$^{-1}$ NMR (CDCl$_3$): δ 8.09 (dd, J=8, J=1.65, 1H), 8.04 (d, J=1.65, 1H), 7.39 d, J=8, 1H), 1.40 (s, 6H), 1.39 (s, 6H)

Compound V—Methyl 4(1',1',3',3'-Tetramethyl-2'-keto-indan-5'-carboxamido)benzoate

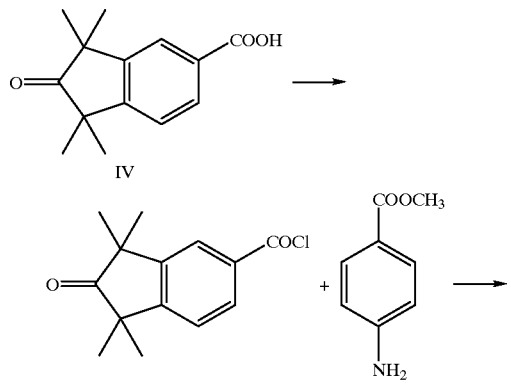

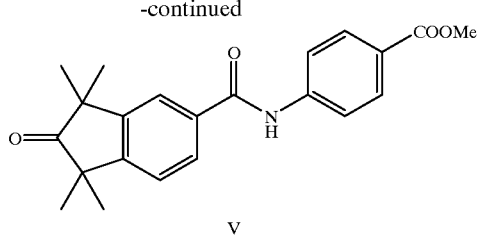

Compound IV (1.1 gms) is suspended in 25 mL methylene chloride and 0.6 mL oxalyl chloride is added, followed by a few drops of DMF (dimethylformamide). The reaction mixture is stirred at room temperature for a few minutes after the reaction subsides, then the solvent is removed in vacuo, the residue is dissolved in 20 mL pyridine, 700 mg methyl p-aminobenzoate is added and the final mixture stirred at room temperature for 16 hrs. The pyridine is then removed in vacuo and the residue is partitioned between water and ethyl acetate. The organic layer is extracted 6 times with 1 N HCl solution, then washed with Na$_2$CO$_3$ solution and saturated NaCl, dried over MgSO$_4$, filtered, evaporated, and the residue purified by column chromatography on silica gel in 25% ethyl acetate/hexane. The main component with R$_f$=0.3 is collected to give 715 mg off-white solid (V).

Infrared spectrum (KBr pellet): 3318, 2967, 1750, 1725, 1640, 1560, 1281 cm$^{-1}$ NMR (CDCl$_3$): δ 8.08 (d, J=6.7, 2H), 7.94 (d, J=1, 1H), 7.80 (dd, J=8, J=1, 1H), 7.75 (d, J=6.7, 2H), 7.40 (d, J=7.7, 1H), 3.93 (s, 3H), 1.40 (s, 6H), 1.38 (s, 6H) Mass spectrum: M/Z=365

Compound VI—4(1',1',3',3'-Tetramethyl-2'-keto-indan-5'-carboxamido)benzoic acid

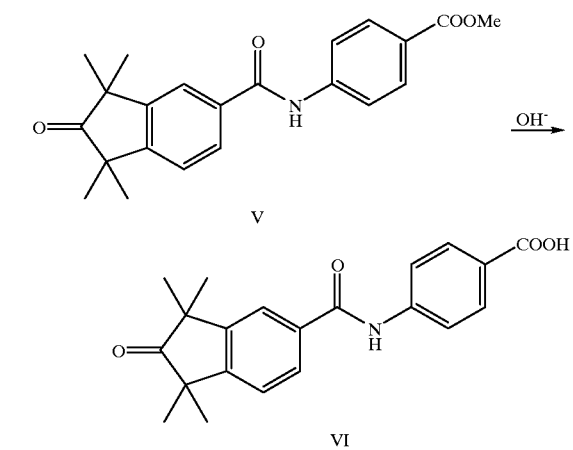

Compound V (700 mg) is dissolved in 90 mL warm methanol, then 6 mL 1 N NaOH is added and the resulting solution refluxed for 4 hours. The solvent was evaporated off, the residue was dissolved in water and the aqueous solution was washed with ether, then acidified with concentrated HCl, the precipitated acid extracted into ethyl acetate, washed with saturated NaCl, dried over MgSO$_4$, filtered, evaporated, and the solid recrystallized from methanol/water. Yield 450 mg white needles (VI). M.p 267–267.5° Thin layer chromatography (30% ethyl acetate/hexane+1% formic acid on silica gel) showed a single component of R$_f$ 0.25.

Infrared spectrum (KBr pellet): 3439, broad absorption 3500–2500, 2960, 1750, 1682, 1607, 1518 cm$^{-1}$ NMR (CDCl$_3$): δ 7.95 (m, 6H), 7.58 (d, J=8, 1H), 1.34 (s, 6H), 1.31 (s, 6H) Elemental analysis: Calculated C 71.78, H 6.02, N 3.99, O 18.21%. Found C 71.85, H 6.05, N 4.01, O 18.09 (diff) %. Mass spectrum: M/Z=351

EXAMPLE 2

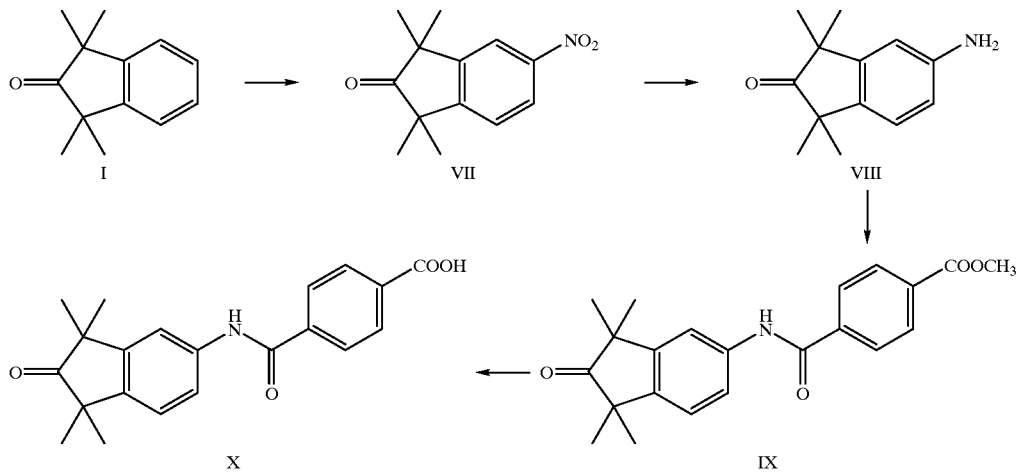

Description of Synthesis

Compound I (1,1,3,3-Tetramethylindan-2-one), is known in the literature (E. Langhals and H Langhals, *Tet Lett* 1990, vol 31, pg 859 and H A Bruson et al, *J Amer Chem Soc* 1958, vol 80, pg 3633). I is nitrated to give VII, which is then catalytically reduced to give amine VIII. VIII is condensed with commercially available methyl 4-(chloroformyl) benzoate to give amide-ester IX, which is hydrolyzed with base to give final compound X.

Compound VII—5-Nitro-1,1,3,3-tetramethyl indan-2-one

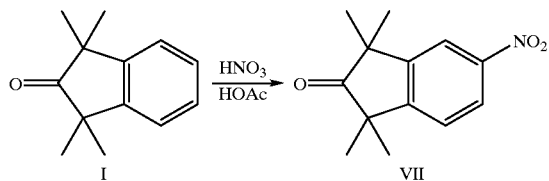

To a mixture of 0.67 mL fuming nitric acid and 0.25 mL acetic acid cooled to 0° was added 255 mg I and the mixture was stirred for 1½ hours, then poured slowly into 50 mL water. The mixture was neutralized by the addition of $Na_2CO_3$, then the organic components were extracted into ethyl acetate, which was washed with saturated NaCl solution, dried over $MgSO_4$, filtered, evaporated, and purified by column chromatography (10% ethyl acetate/hexane on silica gel) to give 199 mg white solid (VII). Thin layer chromatography (10% ethyl acetate/hexane) shows single component $R_f$ 0.45.

Infrared spectrum (KBr pellet): 2971, 1748, 1524, 1460, 1346 $cm^{-1}$ NMR ($CDCl_3$): δ 8.17 (dd, J=8.3, J=2, 1H), 8.12 (d, J=2, 1H), 7.41 (d, J=8.3, 1H), 1.38 (s, 6H), 1.36 (s, 6H) Mass spectrum: M/Z=233

Compound VIII—5-Amino-1,1,3,3-tetramethylindan-2-one

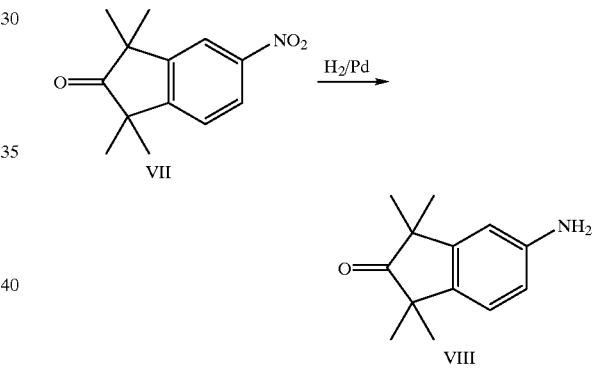

Compound VII (195 mg) was dissolved in 40 mL ethyl acetate and hydrogenated over 80 mg 10% Pd/C for 5 hrs (60 psi $H_2$). The catalyst was filtered off, and the solvent evaporated. Yield 166 mg cream-colored solid (VIII). Thin layer chromatography (10% ethyl acetate/hexane) shows single component Rf 0.1.

Infrared spectrum (KBr pellet): 3472, 3385, 2963, 1746, 1620, 1495 $cm^{-1}$ NMR ($CDCl_3$): δ 7.04 (d, J=8, 1H), 6.66 (dd, J=8, J=2.2, 1H), 6.60 (d, J=2.2, 1H), 1.28 (s, 6H), 1.27 (s, 6H) Mass spectrum: M/Z=203

Compound IX—Methyl 4((1',1',3',3'-tetramethyl-2'-keto-indan-5'-yl-amino)carbonyl)benzoate

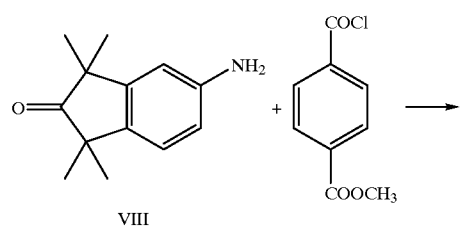

-continued

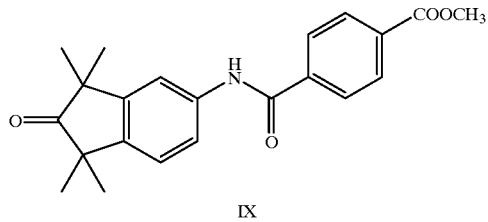

To a solution of 166 mg VIII and 0.5 mL triethylamine in 10 mL ethyl acetate was added 183 mg terephthalic acid monomethyl ester chloride and the reaction was stirred at room temperature for 16 hrs. The precipitated solid was filtered off and discarded. The solvent was evaporated and the residue purified by column chroma-tography on silica gel (20% ethyl acetate/hexane), collecting the main component at $R_f$ 0.2. Yield 245 mg yellow solid (IX).

Infrared spectrum (KBr pellet): 3279, 2965, 1750, 1719, 1651, 1537, 1283, 733 cm$^{-1}$ NMR (CDCl$_3$): δ 8.17 (d, J=8.5, 2H), 7.94 (d, J=8.5, 2H), 7.69 (d, J=2.9, 1H), 7.47 (dd, J=8.2, J=2.9, 1H), 7.28 (d, J=8.2, 1H), 3.96 (s, 3H),1.36 s, 6H), 1.34 (s, 6H) Mass spectrum: M/Z=365

Compound X—4((1',1',3',3'-tetramethyl-2'-keto-indan-5'-yl-amino)carbonyl)benzoic acid

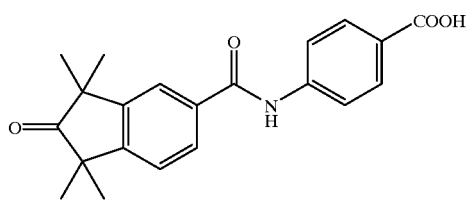

To a solution of compound IX (450 mg) in 25 mL methanol was added 2 mL 1 N NaOH and the mixture refluxed for 20 minutes. The solvent was evaporated off, and the residue was partitioned between ethyl acetate and water. The aqueous phase was separated, acidified with concentrated HCl, and the precipitated solid was extracted into ethyl acetate. The ethyl acetate was dried over MgSO$_4$, filtered, and evaporated. The residual solid was crysallized from methanol/water to give 337 mg light yellow flakes (X) of m.p. 261–2°. Thin layer chromatography (30% ethyl acetate/hexane+1% formic acid on silica gel) showed a single component of $R_f$ 0.25.

Infrared spectrum (KBr pellet): 3387, broad absorption 3400–2500, 2967, 1740, 1686, 1534 cm$^{-1}$ NMR (CDCl$_3$): δ 13.29 (s, 1H), 10.44 (s, 1H), 8.06 (s, 4H), 7.79 (d, J=1.8, 1H), 7.66 (dd, J=8.3, J=1.9, 1H), 7.38 (d, J=8.3, 1H), 1.27 (s, 6H), 1.26 (s, 6H) Elemental analysis: Calculated C 71.78, H 6.02, N 3.99, O 18.21%. Found C 71.78, H 6.10, N 3.83, O 18.29 (diff) %. Mass spectrum: M/Z=351

We claim:

1. A compound of the formula

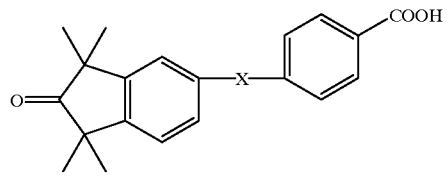

wherein X is —CONH— or —NHCO—, or a nontoxic pharmaceutically acceptable salt, physiologically hydrolyzable ester or solvate thereof.

2. The compound of claim 1 having the formula

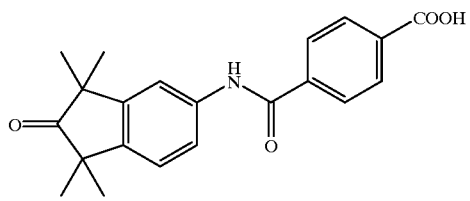

or a nontoxic pharmaceutically acceptable salt, physiologically hydrolyzable ester or solvate thereof.

3. The compound of claim 1 having the formula or a nontoxic pharmaceutically acceptable salt, physiologically hydrolyzable ester or solvate thereof.

4. A pharmaceutical composition comprising a therapeutically effective amount of a compound of claim 1 and a pharmaceutically acceptable excipient.

5. A method of treating a tumor in a mammalian host comprising administering to said host a therapeutically effective amount of a compound of claim 1.

6. A method of treating inflammatory and rheumatic diseases which comprises administering to a mammalian host in need of such treatment an effective amount of a compound of claim 1.

7. A method of treating nonmalignant proliferative skin diseases which comprises administering to a mammalian host in need of such treatment an effective amount of a compound of claim 1.

* * * * *